United States Patent
Kwon et al.

(10) Patent No.: US 9,732,315 B2
(45) Date of Patent: Aug. 15, 2017

(54) AXENIC INOCULATION SYSTEM FOR MICROALGAE USING TR TUBE OF TRIIODIDE RESIN AND METHOD FOR CULTURING AXENIC CULTURE

(71) Applicant: ADVANCED BIOMASS R&D CENTER, Daejeon (KR)

(72) Inventors: Jong Hee Kwon, Gwangju (KR); Ji Won Yang, Daejeon (KR); Ju Young Jung, Ulsan (KR); Gi Bok Nam, Hwaseong-si (KR); Min Sung Park, Daejeon (KR); Nam Kyu Kang, Seoul (KR); Min Gyu Sung, Daegu (KR)

(73) Assignee: Advanced Biomass R&D Center, Daejeon (KR)

( * ) Notice: Subject to any disclaimer, the term of this patent is extended or adjusted under 35 U.S.C. 154(b) by 48 days.

(21) Appl. No.: 14/900,062

(22) PCT Filed: Sep. 5, 2013

(86) PCT No.: PCT/KR2013/008012
§ 371 (c)(1),
(2) Date: Dec. 18, 2015

(87) PCT Pub. No.: WO2014/204050
PCT Pub. Date: Dec. 24, 2014

(65) Prior Publication Data
US 2016/0145556 A1    May 26, 2016

(30) Foreign Application Priority Data

Jun. 19, 2013 (KR) .................... 10-2013-0070099
Jun. 21, 2013 (KR) .................... 10-2013-0071658

(51) Int. Cl.
*C12M 1/00* (2006.01)
*C12M 1/26* (2006.01)
*C12N 1/12* (2006.01)

(52) U.S. Cl.
CPC ............ *C12M 33/14* (2013.01); *C12M 21/02* (2013.01); *C12M 33/04* (2013.01); *C12N 1/12* (2013.01)

(58) Field of Classification Search
CPC .. C08L 2666/02; C08L 2666/04; C08L 53/02; C08L 21/00; C08L 23/00; C08L 29/00; C08L 33/00; C08L 53/00; C09J 153/02; C09J 121/00; C09J 123/02; C09J 11/04; C09J 133/08; C09J 133/16; C09J 135/06; C09D 153/02; C12M 21/02; C12M 33/04; C12M 33/14; C12N 1/12
See application file for complete search history.

(56) References Cited

U.S. PATENT DOCUMENTS

| | | | | |
|---|---|---|---|---|
| 4,238,477 A | * | 12/1980 | Lambert | ................. A01N 59/12 |
| | | | | 210/501 |
| 2010/0190227 A1 | * | 7/2010 | Dauth | .................... C12M 21/02 |
| | | | | 435/168 |
| 2012/0077243 A1 | * | 3/2012 | Niazi | ................... B01J 20/2805 |
| | | | | 435/170 |

FOREIGN PATENT DOCUMENTS

| KR | 0079714 A | * | 8/2001 |
|---|---|---|---|
| WO | 2011159709 | * | 12/2011 |

* cited by examiner

*Primary Examiner* — Debbie K Ware
(74) *Attorney, Agent, or Firm* — Medler Ferro Woodhouse & Mills PLLC (57) ABSTRACT

A triiodide resin (TR) tube of the present invention has a cylindrical shape. A resin exhaust preventing part is provided at a lower portion of the TR tube, and a triiodide resin is received inside the TR tube. A contaminated culture passes through the TR tube to allow an axenic culture to flow out. When a microalgae culture contaminated with bacteria passes through the TR tube filled with the triiodide resin, a pure culture of microalgae can be prepared by using the sterilizing rate of bacteria populations, which is relatively higher than that of microalgae, due to characteristics of iodine exhibiting negative polarity. An axenic inoculation system for microalgae using the TR tube of the present invention comprises the steps of: sterilizing a photobioreactor (PBR) with peracetic acid, washing the PBR with purified water, and filling the PBR with a sterilized culture; allowing a microalgae culture contaminated with bacteria to pass through a TR tube attached on an upper portion of the PBR, thereby obtaining an axenic culture; and inoculating the axenic culture into a culture liquid inside the PBR to culture microalgae. According to the present invention, the microalgae contaminated with bacteria are sterilized together with bacteria in external air flowing in the TR tube while passing through the TR tube, thereby causing no secondary contamination at the time of inoculation or culture.

10 Claims, 7 Drawing Sheets

AXENIC INOCULATION SYSTEM FOR MICROALGAE USING TR TUBE OF TRIIODIDE RESIN AND METHOD FOR CULTURING AXENIC CULTURE

TECHNICAL FIELD

The present invention relates to an axenic inoculation system for microalgae using a triiodide resin (TR) tube of a triiodide resin, and a method for culturing an axenic culture. More particularly, a TR tube is fabricated using a triiodide resin and a method for culturing an axenic culture. More particularly, a TR tube is fabricated using a triiodide resin and attached on an upper portion of a photobioreactor (PBR), and used for passing a culture solution containing microalgae, pure liquid and air through the TR tube. The present invention relates to an axenic inoculation system for microalgae using the TR tube which principally prevents contamination with bacteria possibly occurred due to temporary exposure to external environments at the time of inoculation of microalgae during culture, while selectively passing air, the culture and microalgae only through a closed photobioreactor (PBR). Accordingly, the present invention relates a configuration of a selective channel for selectively preventing and sterilizing inflow of bacteria parasitic everywhere, and an axenic inoculation system using the same. Further, the present invention relates to an economical and novel process with simplicity in operation and enabling sterilization in a short time by using a sterilizing rate of bacteria populations, which is relatively higher than that of microalgae, due to characteristics of iodine exhibiting negative polarity when the microalgae contaminated with bacteria pass through a TR tube filled with triiodide resin to selectively choose the microalgae contaminated with bacteria, thereby producing a pure culture of microalgae.

BACKGROUND

One of solutions for stable mass-production of biodiesel using microalgae is to use a culture system having a closed photobioreactor (PBR) with the purpose of maximally increasing a biomass concentration under optimum operational conditions for cell growth of microalgae and through a stable control thereof. In other words, the culture system is a system to execute the culture by stably culturing the biomass produced in the PBR in order to derive lipid accumulation in cells, thereby maximizing lipid productivity (g/m$^2$/yr). The PBR may culture the microalgae with a high efficiency and prevent direct contact the same with external environments during culturing, therefore, have a lower probability of contamination with external bacteria, compared to an open pond. However, there is still a possibility of contamination with bacteria due to temporary exposure to the external environments possibly occurred when the inoculation is conducted during indoor/outdoor culture exposed to the external environments. There have been a number of studies that examined microbial sterilization, water treatment performance and stability of a triiodide anion exchange resin, which is also used in the present invention. However, the present invention primarily proposes an application of a safe axenic inoculation of microalgae in an external exposure manner outside the PBR.

In an industrial applicability including the production of a biodiesel obtained through the culture of microalgae and development of novel bioactive materials, it is very important to maintain a pure culture in aspects of genetic engineering and/or findings of inherent features of microorganisms.

Microalgae present in a natural state mostly co-exist with or are parasitic on various species of bacteria, however, studies into a biological interrelation between the microalgae and the bacteria are still not known in the art.

The triiodide anion exchange resin used in the present invention is one of halogen compounds, and a number of studies on high microbial sterilization, water treatment performance and stability of the above resin have been conducted. However, using the triiodide anion exchange resin to prepare a pure culture of microalgae as the present invention will be a novel application.

DISCLOSURE

Technical Problem

The PBR is prevented from direct contacting with external environments, however, it cannot be excluded a possibility of contamination with bacteria due to temporary exposure to the external environments possibly occurred during inoculation of bacteria species in indoor/outdoor cultures. Accordingly, from the microalgae contaminated in the indoor/outdoor cultures or after sterilizing bacteria existing in the external environments, axenic microalgae only must selectively pass through a TR tube then be inoculated in the PBR.

In order to select the microalgae contaminated with bacteria and prepare a pure culture, there are conventional methods for separation of microalgae, for example, administration of antibiotics to a medium, direct separation after microscopic observation, and preparation of a colony on an agar plate. However, among these conventional methods, the colony selection method has a difficulty since the microalgae have a lower growth rate than that of bacteria, the use of antibiotics is limitedly applied to strains since it may involve a possibility of affecting bioactivity of desired strains, and has low efficiency in terms of costs and time. Further, in the case of the direct separation method, it is often impossible to prepare and select a pure culture depending upon types of microalgae (size and shape) and due to generation of neighboring groups due to viscosity of the bacteria.

Technical Solution

The method of the present invention includes: sterilizing a PBR with peracetic acid, washing the PBR with purified water; and passing a microalgae culture contaminated with bacteria through an open TR tube installed at an upper portion of the PBR to obtain an axenic culture, and then, inoculating the axenic culture in a culture solution inside the PBR to culture microalgae. Accordingly, an object of the present invention is to provide an axenic inoculation system for microalgae using a TR tube by feeding air for PBR and the axenic culture of the microalgae into the PBR.

The axenic inoculation system for microalgae using the open TR tube of the present invention is an axenic system having the open TR tube to connect inside and outside of a bioreactor, and may allow feeding of additional culture solution and other liquid components from the outside through the open TR tube without a risk of contamination, since a triiodide resin has selective extinction performance of bacteria strains.

A principle of a technical configuration of the present invention is that a pure culture of microalgae may be produced by using a sterilizing rate of bacteria populations, which is higher than that of the microalgae, due to characteristics of iodine exhibiting a negative polarity, when the microalgae culture contaminated with bacteria pass through a column filled with the triiodide resin. The present invention needs about 10 minutes to prepare the pure culture, therefore, may be very efficient in terms of time. Further, since the column may be continuously reused after washing, the present invention also has an economical advantage and simplicity in operation.

Advantageous Effects

The present invention may principally prevent bacterial contamination possibly occurred by temporary exposure of microalgae to external environments during inoculation, and provide air, a culture and the microalgae to a PBR through an open TR tube in axenic state. Further, since no thermal or chemical method is used for sterilization of the culture, energy consumption is small. In addition, since sterilization may be completed in a short time, the axenic culture becomes simple, and thereby providing a continuous axenic process system.

BEST MODE

Figure 7:
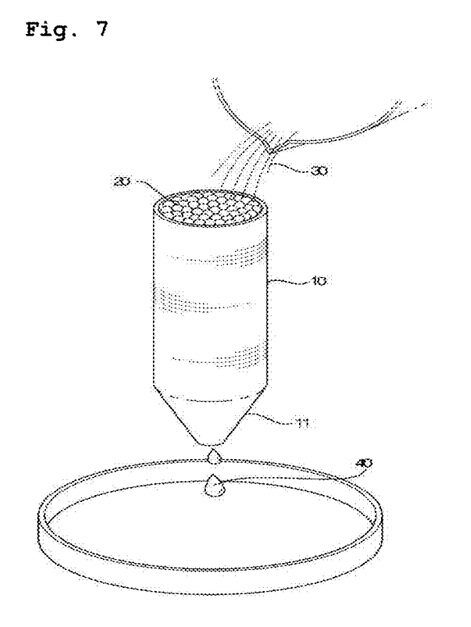
FIG. 7 is a perspective view illustrating a state of using a TR tube according to the present invention (10: TR tube, 11: taper part, 20: TR resin, 30: contaminated culture, 40: axenic culture)
Figure 8:
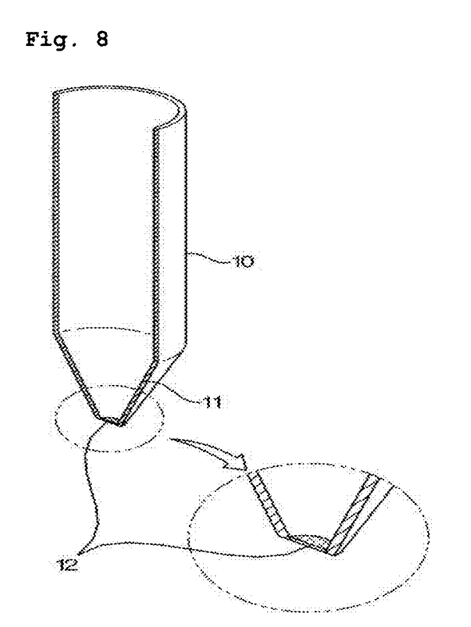
FIG. 8 is a partial sectional view of the TR tube (10: TR tube, 11: taper part, 12: resin discharge prevention part)

The TR tube containing a triiodide resin may have a barrel shape with a convex bottom to receive a TR resin (with a size of 2 cm diameter×7 cm height in the present invention, however, the size of TR tube is not significant), and a resin discharge prevention part is formed at a lower portion of the TR tube to prevent outflow of the resin while passing the microalgae culture through the triiodide resin to flow out. In addition, the TR tube includes a taper part (reduced diameter part') formed at the lower portion thereof with a decreased cross-sectional area, and the resin discharge prevention part may be provided in a form of hole or net at an exit of the lower part. The hole or net in the resin discharge prevention part of the TR tube may be made of iron, ceramic, plastic or a synthetic fiber.

After passing the contaminated culture through the TR tube once, twice or more, about 20 ul of the solution having passed through the TR tube was smeared on LB agar and TYG agar plates and incubated at room temperature for 30 hours. Thereafter, the number of the generated bacteria colonies was counted to identify bacteria extinction effects of the triiodide resin.

The TR tube may be set to have a sufficient treatment capacity at one time with a high feed rate by adjusting a diameter size and a length of the tube and controlling a connection method in a module type, and may be installed in a channel form at the upper portion of the PBR and utilized as a passage required for inoculating the microalgae. Further, the TR tube may also be used as a pathway for air balance in the bioreactor, which is needed during harvesting biomass.

The system of the present invention is configured to: sterilize a PBR with peracetic acid and wash the same with purified water; pass a microalgae culture contaminated with bacteria through an open TR tube installed at the upper portion of the PBR to obtain an axenic culture; and inoculate the axenic culture in a culture solution inside the PBR to culture microalgae. Accordingly, the present invention provides an axenic inoculation system using the TR tube by feeding the axenic culture of microalgae to the PBR.

EXPERIMENTAL EXAMPLE

1) Material and Apparatus

*Nannochloropsis gaditana* culture contaminated with bacteria, a cylindrical TR tube (conical, 2×7 cm) without particular limitation in a size thereof, a triiodide resin, a petri dish, a tryptone-yeast extract-glucose (TYG) agar medium, and an LB agar medium.

2) Selective Death of Bacteria

A small exit was formed in a bottom of a barrel tube having a diameter of 2 cm, which is filled with a triiodide resin, and a resin discharge prevention part (using a small wire mesh) was provided in order to prevent outflow of the resin while allowing a microalgae culture to pass through the triiodide resin to flow out. After passing *N. gaditana* culture contaminated with a number of bacteria through the prepared triiodide resin for 0, 1 and 2 times, about 20 ul of the solution having passed was smeared on each of LB agar and TYG agar plates and incubated at room temperature for 30 hours, followed by counting the number of generated bacteria colonies to identify bactericidal effects of the triiodide resin. As compared to bacteria, the microalgae has a stronger cell wall which exhibits a negative charge, therefore, it is expected that a decrease in the number of microalgae populations is relatively lower than that of bacteria due to a statistic repulsive force between the microalgae and the triiodide resin.

3) Culture of Microalgae

Strains: *Nannochloropsis gaditana* strain Medium: F/2 medium

Material and apparatus: 250 ml baffled flask, an LED, 2% $CO_2$, a PTFE air filter (0.45 m, Corning, United States), and a UV/Vis spectrometer (Shimadzu, Japan)

Method: After inoculating *N. gaditana* culture, which was filtered by passing the same through a column filled with a triiodide resin once or twice, on f/2 medium in a sterilized flask, the culture was incubated at room temperature while injecting 2% $CO_2$. Growth of the microalgae was subjected to sampling every 12 hours and observed from absorbance at wavelengths of 750 nm and 680 nm using the UV/Vis spectrometer. A degree of bacterial contamination of the microalgae in a liquid broth was investigated through direct microscopic observation.

Example 1

Culture Solution and Sterilization of Contaminated Culture

In a cylindrical TR tube having a diameter of about 2 cm, which is filled with a triiodide resin, a wire mesh having a smaller pore size than a glass bead was spread to prevent outflow of the resin (TR) while stacking the triiodide resin up to a height of 8 cm. Then, the TR tube was installed at the upper portion of a PBR. By passing *N. gaditana* preculture contaminated with bacteria through an open TR tube (triiodide resin), the preculture was inoculated with the culture solution in the PBR.

Figure 1:
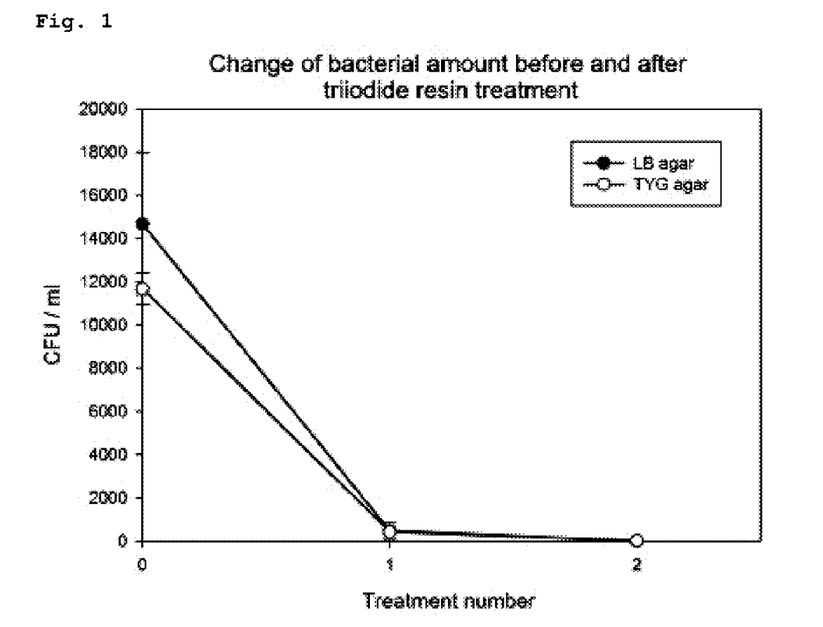
FIG. 1 is a diagram illustrating a change in an amount of bacteria before/after treatment using a triiodide resin.
Figure 2:
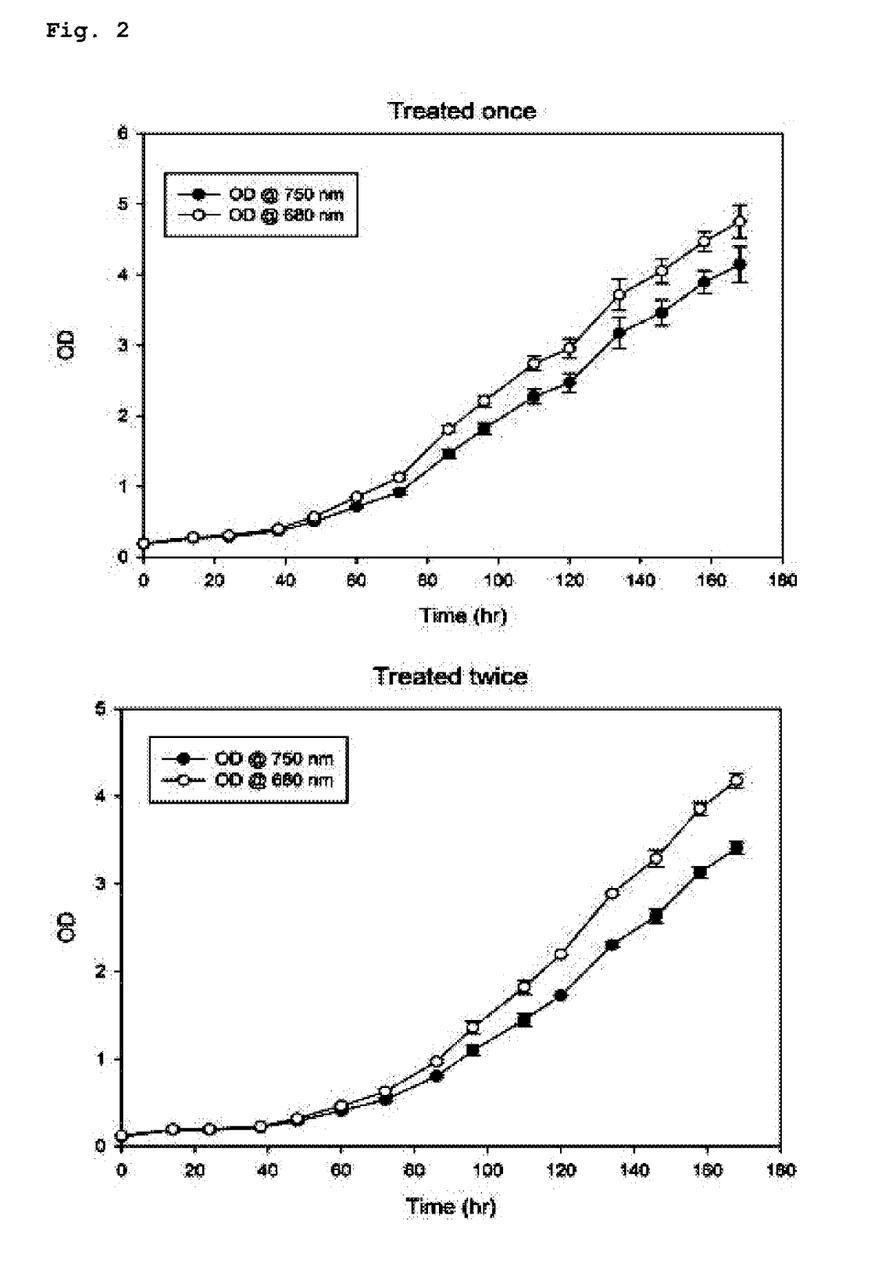
FIG. 2 is diagrams illustrating a change in growth of *N. gaditana* after removal of bacteria once and twice.
Figure 3:
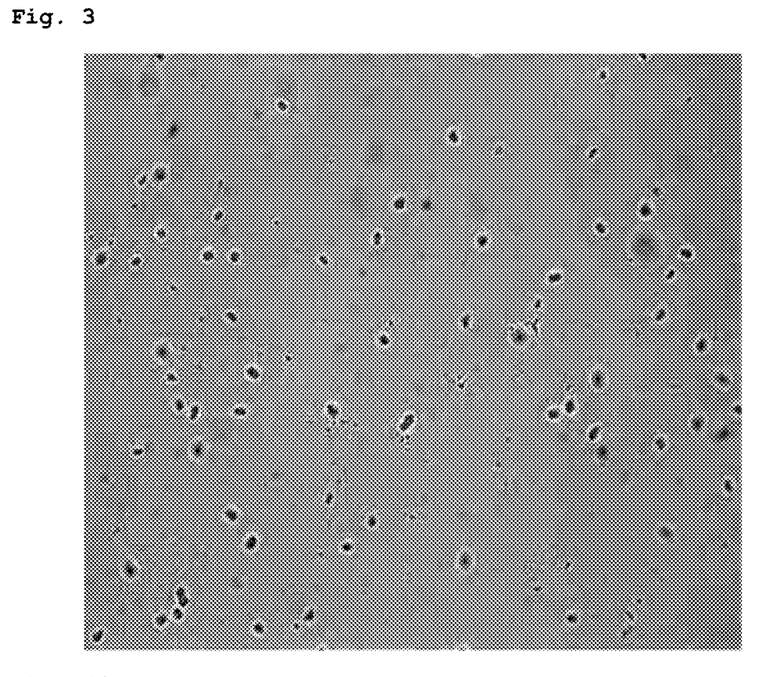
FIG. 3 is a photograph of contaminated *N. gaditana* cell.
Figure 4A:
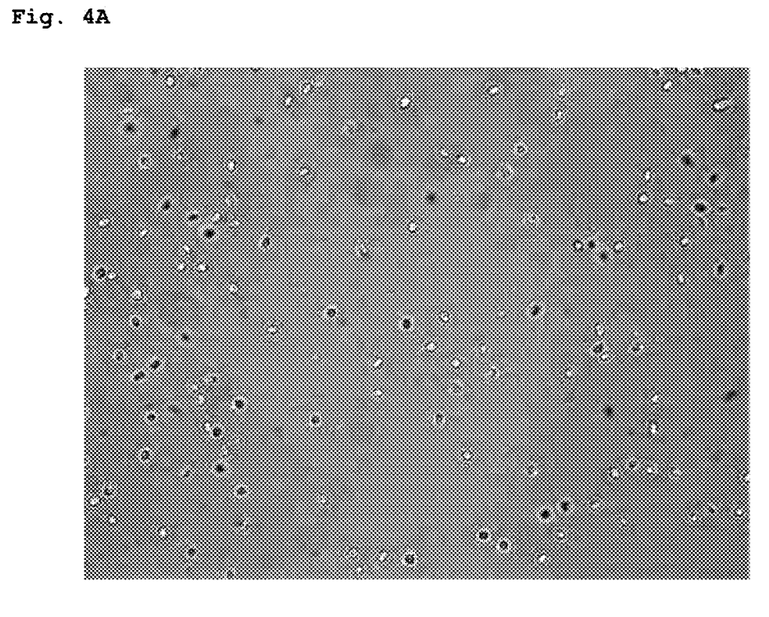
FIG. 4A is a photograph of *N. gaditana* cell after treatment once.
Figure 4B:
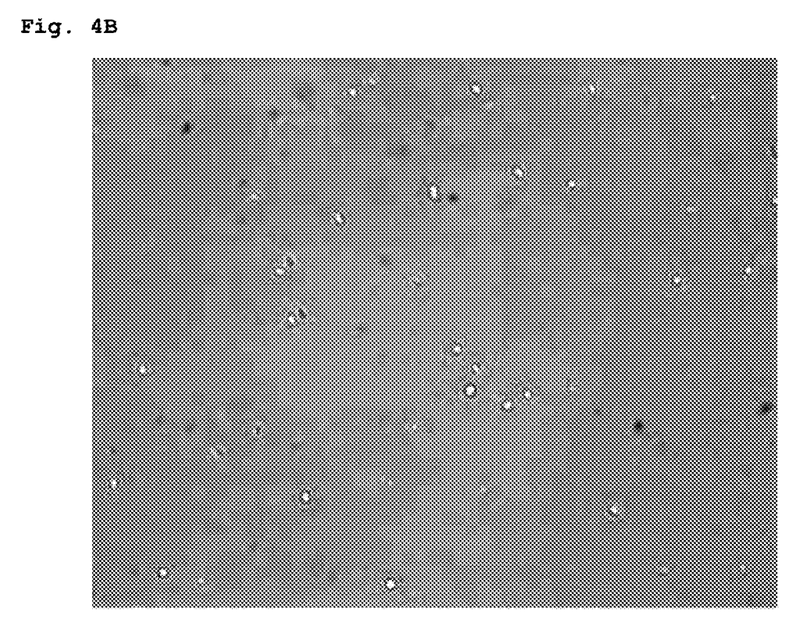
FIG. 4B is a photograph of *N. gaditana* cell after treatment twice.
Figure 5:
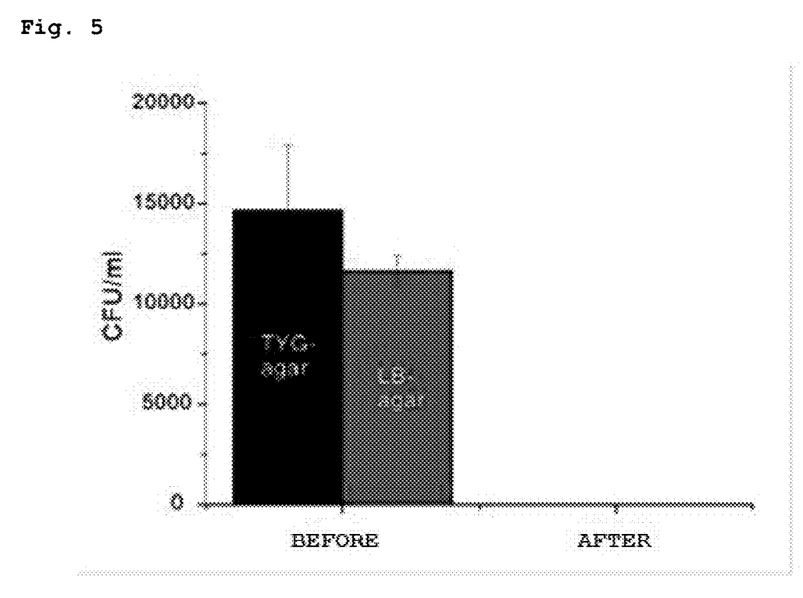
FIG. 5 is a diagram illustrating experimental results proving bacterial sterilization.
Figure 6A:
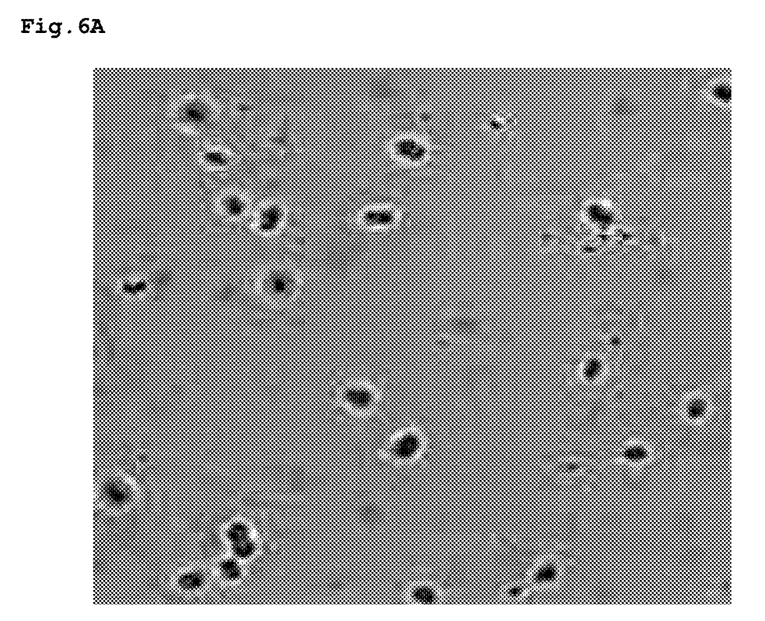
FIG. 6A is a micrograph before treatment (from preculture).
Figure 6B:
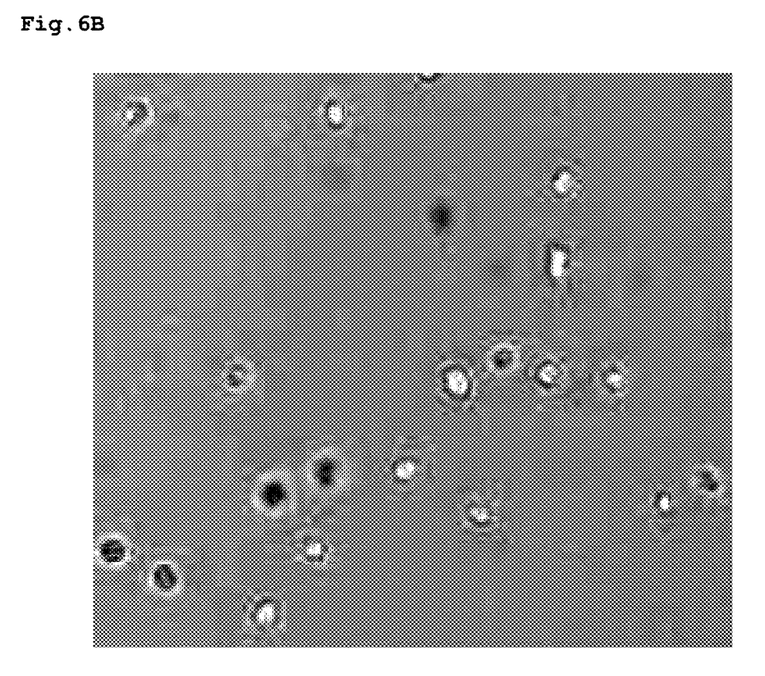
FIG. 6B is a micrograph after treatment (from photobioreactor (PBR)).

Due to high adhesion of the triiodide resin to bacteria and sterilization ability thereof, microorganisms except for the microalgae were not found inside the reactor and the microalgae could be cultured in a single strain state. A sample before the inoculation (contaminated preculture) and another sample in the reactor after the inoculation through the TR tube were taken, and bacteria populations contained therein were smeared on each of TYG and LB agar media and compared to each other (FIG. 1). Although the number of strains before treatment was 15,000 CFU/ml in the TYG agar medium, the medium was monitored to be axenic after treatment. Further, the number of strains in the LB agar medium was 12,000 CFU/ml before treatment, however, the medium was also axenic after treatment. These results are obtained because the microalgae selectively passed through the TR tube and were grown up while the bacteria could not almost pass through the same, and even some passed bacteria were almost 100% dead, due to the negative polarity and sterilization ability of iodine.

Example 2

Culture of Microalgae

Figure 9:
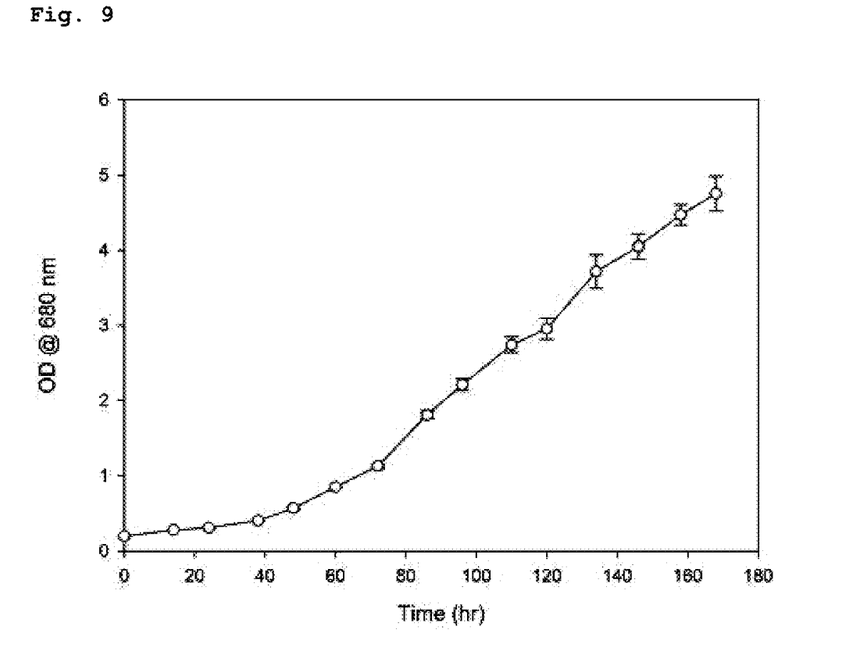
FIG. 9 is a diagram illustrating a growth curve of microalgae in the PBR.
Figure 10:
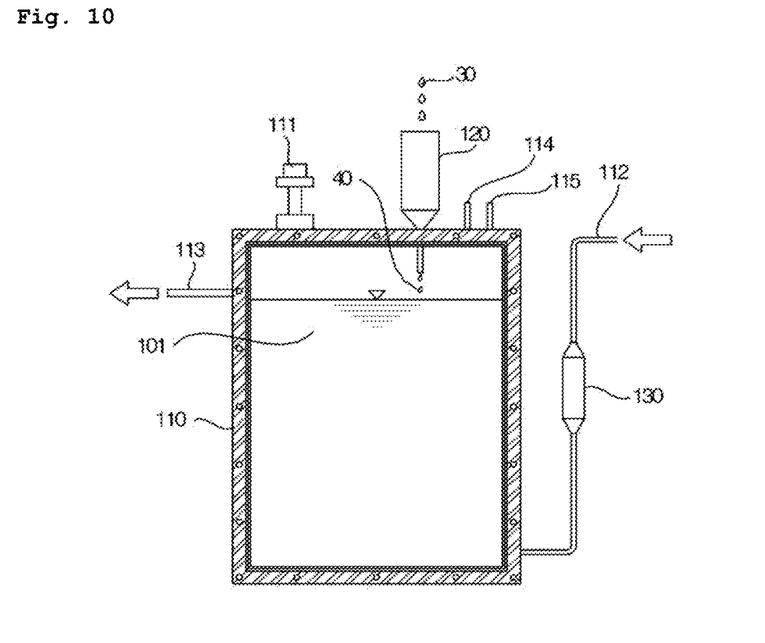
FIG. 10 is a view illustrating an apparatus of the present invention (101:
culture solution, 40: axenic culture, 110: PBR, 111: pH sensor, 112: inlet, 113: outlet, 114: NaOH inlet, 115: HCl inlet, 120: open TR tube, 130: medium).

In the PBR (FIG. 10), *Nannochloropsis gaditana* strains were inoculated on the medium (F/2 medium). F/2 medium consisted of $8.83 \times 10^{-4}$ M $NaNO_3$, $3.63 \times 10^{-5}$ M $NaH_2PO_4$, $1.07 \times 10^4$ M $Na_2SiO_3$, $1 \times 10^{-5}$ M $FeCl_3$, $1 \times 10^{-5}$ M $Na_2$ EDTA, $4 \times 10^{-8}$ M $CuSO_4$, $3 \times 10^{-8}$ M $Na_2MoO_4$, $8 \times 10^{-8}$ M $ZnSO_4$, $5 \times 10^{-8}$ M $CoCl_2$, $9 \times 10^{-7}$ M $MnCl_2$, $1 \times 10^{-10}$ M Vitamin $B_{12}$, $2 \times 10^{-9}$ M Biotin, and $3 \times 10^{-7}$ M Thiamine. In order to culture the microalgae, the material and apparatus includes 2 L flat type fluorescent bioreactor, an LED light source, 2% $CO_2$, a PTFE air filter (0.45 m, Corning, United States). Growth of *N. gaditana*, which was inoculated using a triiodide resin, was observed by using a UV/Vis spectrometer (Shimadzu, Japan) through absorbance at a wavelength of 680 nm (FIG. 9). The degree of bacterial contamination of the microalgae in a liquid phase was investigated through direct microscopic observation (FIGS. 6A and 6A), and results thereof are shown in FIGS. 5, 6A, 6B and 9.

Test Example 1

A change in the number of bacteria populations decreased when passing the microalgae culture contaminated with bacteria through the triiodide resin is indicated as a change in the number of colonies. Even if the microalgae passed through both types of media (LB agar and TYG agar) only once, a bacteria removal efficiency of 99% or more was exhibited. When passing the microalgae through the media twice or more, sterilization effect reached substantially 100%.

Test Example 2

When passing the microalgae through a triiodide resin column twice, 100% bacteria were removed. However, in a case of the microalgae, that is, *N. gaditana*, the number of populations is reduced as the number of passing the triiodide resin is increased. However, it could be seen from the microscopic observation and measurement of a cell optical density that a large number of the populations are still alive, cultured and grown as a pure culture. The wavelength of 750 nm was used as an indicator to measure the number of cells in the microalgae, while the wavelength of 680 nm became an indicator to approximately measure a content of chlorophyll in the microalgae. It could be observed that a predetermined pattern existed between an increase at 750 nm and an increase at 680 nm.

The present invention has succeeded to prepare the axenic microalgae by using a sterilization rate of bacteria populations, which is relatively higher than that of the microalgae, due to characteristics of iodine exhibiting negative polarity when the microalgae culture contaminated with bacteria passed through a column filled with a triiodide resin. In this regard, a time required for the same was approximately 10 minutes, therefore, may be highly efficient in terms of time, as compared to any conventional method for preparing an axenic culture. Further, since the column can be continuously reused after washing, the present invention has an economical advantage and simplicity in operation.

Test Example 3

Death of Bacteria

The numbers of bacteria populations before and after passing the microalgae preculture contaminated with bacteria through the triiodide resin were compared. A sample of the preculture after passing the triiodide resin was directly taken from the PBR in order to further prove that the inside of the PBR was kept to be axenic without bacteria. The microalgae are slowly grown in the agar medium, compared to the bacteria, therefore, does not form a colony until the colony of bacteria is exhibited. With two types of agar media used in the present test (LB and TYG agar), it was found that bacteria had been completely dead when the inoculation was conducted using the triiodide resin. Accordingly, it was demonstrated that external bacteria cannot flow into the bioreactor even by passing contaminated biomass for inoculation through the TR tube (FIGS. 4, 5, 6 and 9).

INDUSTRIAL APPLICABILITY

After selecting microalgae contaminated with bacteria through the open TR tube of the present invention, 100% of the bacteria may be completely sterilized and inflow of bacteria existing in an external air inside the bioreactor may be principally prevented. Further, in the case of inoculating or culturing after sterilization, there is no risk of secondary contamination, and thereby enabling a simple and economical process of working in indoor/outdoor culture. Therefore, the present invention has scholarly and industrial applicability.

DESCRIPTION OF REFERENCE NUMERALS

10: TR tube, 11: taper part, 12: resin discharge prevention part, 20: TR resin, 30: contaminated culture, 40: axenic culture, 101: culture solution, 110: PBR, 111: pH sensor, 112: inlet, 113: outlet, 114: NaOH inlet, 115: HCl inlet, 120: open TR tube, 130: medium.

The invention claimed is:

1. A triiodide resin (TR) tube which has a barrel shape, and includes a taper part at a lower portion thereof with a decreased cross-sectional area, and a resin discharge prevention part provided in an exit at an end thereof.

2. The TR tube according to claim 1, wherein the resin discharge prevention part includes a hole or mesh.

3. The TR tube according to claim 1, wherein the hole or mesh of the resin discharge prevention part is made of iron, ceramic, plastic or a synthetic fiber.

4. The TR tube according to claim 1, wherein the triiodide resin is formed in a spherical shape or granular form having a single diameter or two or more different diameters.

5. The TR tube according to claim 1, wherein the barrel shape includes a cylindrical shape or a polygonal tube shape.

6. A method for culturing axenic culture of microalgae using a triiodide resin, comprising: passing a microalgae culture contaminated with a number of bacteria through a triiodide resin (TR) tube to obtain an axenic culture, wherein the TR tube includes the triiodide resin and has a resin discharge prevention part at a lower portion thereof.

7. The method according to claim 6, comprising: passing the contaminated culture through the TR tube once or more; smearing the culture on a medium; incubating the culture at room temperature to produce bacteria colonies; and counting the number of bacteria colonies to identify death of bacteria.

8. The method according to claim 7, wherein the medium is a LB agar plate and a TYG agar plate.

9. An axenic inoculation system for microalgae using a TR tube, configured to: sterilize a photobioreactor (PBR) with peracetic acid wash the same with purified water, fill the PBR with a sterilized culture; pass a microalgae culture contaminated with bacteria through the TR tube attached to an upper portion of the PBR to obtain an axenic culture; and inoculate the axenic culture in a culture solution inside the PBR to culture microalgae.

10. The axenic inoculation system according to claim 9, wherein the microalgae contaminated with bacteria is sterilized by an open triiodide resin (TR) tube.

* * * * *